(12) United States Patent
Kajimoto et al.

(10) Patent No.: US 6,194,381 B1
(45) Date of Patent: Feb. 27, 2001

(54) THERAPEUTIC AGENT AND METHOD FOR FELINE AIDS VIRUS INFECTIONS AND FELINE ATOPIC DERMATITIS

(75) Inventors: Tsunesuke Kajimoto, Kanagawa (JP); Ryougai Go, Houston, TX (US); Makoto Suzuki, Aichi (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/101,144
(22) PCT Filed: Oct. 30, 1997
(86) PCT No.: PCT/JP97/03963
§ 371 Date: Nov. 19, 1998
§ 102(e) Date: Nov. 19, 1998
(87) PCT Pub. No.: WO98/18484
PCT Pub. Date: May 7, 1998

(30) Foreign Application Priority Data

Oct. 31, 1996 (JP) ................................................ 8-290601

(51) Int. Cl.⁷ ............................. A61K 38/21; C07K 14/55
(52) U.S. Cl. ........................ 514/2; 424/85.4; 424/185.1; 435/69.5; 530/351
(58) Field of Search ........................ 530/351; 536/3.52; 424/185.1, 85.4; 435/69.51; 514/2

(56) References Cited

U.S. PATENT DOCUMENTS 5,194,381 * 3/1993 Yanai et al. ........................ 435/172.3

FOREIGN PATENT DOCUMENTS

WO9603435 * 2/1996 (WO) ............................. C07K/14/57

OTHER PUBLICATIONS

File Caplus on STN. Weetman et al. 'The In Vitro Regulation of Human Tryocyte HLA–DR Antigen Experession', J. Clin. Endocrinol. Metabl. vol. 61, No. 5, pp. 817–824. Abstract only, 1985.*

File Caplus on STN. Tomita et al. 'Effects fo Human .Gamma. Interferon on Clell Growth, Replication of Virus and Induction of 2'–5' Oligoadenylate Synthetase in Three Human Lymphoblastoid Cell Lines and K652 Cells.' Int. J. Cancer. vol. 30, No. 2, pa, 1982.*

* cited by examiner

Primary Examiner—Christopher S. F. Low
Assistant Examiner—Anish Gupta
(74) Attorney, Agent, or Firm—Austin R. Miller

(57) ABSTRACT

A therapeutic agent for feline immunodeficiency virus (FIV) infections, (including the treatment of the anemia and chronic stomatitis caused by infection with a FIV) comprising a feline interferon preparation containing a feline interferon as a principal agent, and a therapeutic method for FIV infections comprising administering a feline interferon preparation containing a feline interferon as a principal agent to a cat every day are disclosed. Furthermore, a therapeutic method and agent for feline atopic dermatitis are disclosed. The preferred feline interferon, is an ω-feline interferon.

9 Claims, No Drawings

THERAPEUTIC AGENT AND METHOD FOR FELINE AIDS VIRUS INFECTIONS AND FELINE ATOPIC DERMATITIS

Therapeutic agent and method for feline AIDS virus infections and feline atopic dermatitis.

1. Technical Field

The present invention relates to a therapeutic agent and method for feline AIDS virus (FIV) infections and feline atopic dermatitis. A FIV belongs to Lentiviridae of Retroviridae, and cats living freely outdoors are often infected with it.

FIV infections are said to undergo three stages; an initial acute stage of virus infection, latent stage, and lastly, a chronic disease stage of immunodeficiency.

In the initial stage of infection, fever and lethargy can be observed, and lymphopenia and neutropenia occur. The skin and digestive tracts can become infected with microbes, but these are secondary infections by neutropenia. Vomition and anemia can also be observed. After the symptoms in the acute stage vanish, the latent stage continues for several months to several years.

In the last stage, chronic diseases such as chronic stomatitis, chronic respiratory organ diseases, anemia, intractable secondary infections and enteritis occur, and the carriers become gradually weak in several years, and finally die. Furthermore, opportunistic infections such as Haemobartonella diseases and Cryptococcus diseases can be seen.

2. Background of the Related Art

Therapy of FIV infections is still untapped, and no therapeutic method has been developed for eliminating FIV, i.e., a retrovirus from the feline body after infection. As therapeutic agents for human AIDS are developed, it can be considered to use them as anti-FIV drugs for cats in the future, but the application of a reverse transcriptase inhibitor such as AZT (azidothymidine) seems problematic for the time being, considering its side effects versus the desired effect to be achieved.

At present, therapeutic methods for symptoms from secondary infections, such as the administration of antibiotics, infusion and blood infusion and administration of steroid hormone preparations are used.

Anemia as one of FIV infections can be seen in the early stage and last stage of FIV virus infection, and at the onset, vitality vanishes and appetite diminishes or is lost. Furthermore, erythroid values such as erythrocyte number, hemoglobin and hematocrit decrease. Symptomatic therapeutic methods such as the administration of erythropoietin and the infusion of vitamins, amino acids, etc., and as the case may be, blood infusion are used. However, most carriers die, though these methods have some macrobiotic effect.

Chronic stomatitis as one of FIV infections is an intractable disease, and the inflammation of the gum near the roots of molar teeth causes heavy swelling, not allowing eating. Weakened cats in this stage come to hospital. Steroid hormone preparations such as Depo-Metrol are administered to temporarily improve the inflammation as a symptomatic therapeutic method. However, the disease recurs in 2 to 3 weeks, and the administration of steroid hormone preparations is practiced again. The recurrence period becomes gradually shorter, and partly because of side effects by steroid hormone preparations, the cats ultimately die.

As a feline interferon, a recombinant ω-interferon preparation is already approved as a therapeutic agent for calicivirus infections, and is marketed under a trade name of "INTERCAT" since Feb., 1994. The inventors studied a therapeutic method for FIV infections using this recombinant ω-interferon, and as a result, completed the present invention.

Presently known interferons include alpha (α) interferons, beta (β) interferon, gamma (γ) interferon, omega (ω) interferon and tau (τ) interferon. As human interferons, three types of α, β and γ are practically applied, and as a feline interferon, an ω-interferon only is practically applied. "INTERCAT" is a recombinant ω-feline interferon preparation, and it is an injection preparation obtained by infecting *Bombyx mori* with a baculovirus recombined with the gene of an 107-feline interferon, producing the interferon in the *Bombyx mori,* extracting and purifying it, adding gelatin and D-sorbitol as a stabilizer and recipient, and freeze-drying the mixture. The recombinant ω-feline interferon is a glycoprotein with a molecular weight of about 25,000, and its protein portion has the amino acid sequence as shown in SEQ ID NO:1 of the sequence listing.

The ω-feline interferon can also be produced by other methods than the *Bombyx mori* method. For example, it can be produced by transient expression methods using animal cells such as simian COS cells and gene recombination techniques using Chinese hamster ovary (CHO) cells, Escherichia coli, yeast, transgenic animals, etc.

As for the usage and dose of "INTERCAT" approved as a therapeutic agent for calicivirus infections, it is specified to administer 2.5~5 MU/kg of feline interferon intravenously three times every other day. In this case, MU (mega unit) is a method for expressing a titer with the antiviral activity of an interferon as an indicator, and expresses one million units. The inventors attempted to treat FIV infections, particularly anemia and chronic stomatitis, according to the same usage and dose of every-other-day administration as approved for treating calicivirus infections, but the expected effects could not be obtained. So, the inventors continued their studies by changing the usage and dose.

A task of the present invention is to provide a new excellent therapeutic agent and method for FIV infections.

On the other hand, for feline atopic dermatitis, there is no satisfactory therapeutic method even for human atopic dermatitis. Symptomatic therapeutic methods using steroid hormone preparations are frequently adopted. Steroid hormone preparations have side effects, and the symptomatic therapeutic methods are insufficient in therapeutic effect. Feline atopic dermatitis is an intractable disease. Generally observed feline allergic dermatitis is mostly atopic dermatitis including miliary eczema relating to parasites (such as fleas) and eosinophilic granuloma syndrome. Hitherto, drugs such as prednisolone and amcinolone are said to be effective, and they tend to be used more frequently. However, these drugs have the problem of side effects.

It was reported in an American medical magazine in 1990 (M. Boouniewwicz et al., American J. Medicine, 8.8, 365–370 (1990)) that a human γ(gamma) interferon is effective for human atopic dermatitis.

However, this method is not sufficient in the effect of treating feline atopic dermatitis since human interferons are different in their action than feline interferons.

Another object of the present invention is to provide a new excellent therapeutic agent and method for feline atopic dermatitis.

Disclosure of the Invention

The inventors studied to achieve the above objectives, and as a result, found a therapeutic method for FIV infections by injecting a therapeutic agent containing a feline ω-interferon into cats.

An effective therapeutic method has been invented, in which the anemia and chronic stomatitis caused by infection with a FIV (confirmed to be positive in anti-FIV antibody by virus tests of feline blood) are treated by using a therapeutic agent containing a feline ω-interferon.

Furthermore, it has been found that a therapeutic agent containing an (ω-feline interferon is a new excellent therapeutic agent for feline atopic dermatitis.

The following objectives of the present invention have been industrially advantageously achieved by the present invention with the following constitution:

[1] A therapeutic agent for FIV infections, comprising a feline interferon preparation containing a feline interferon as a principal agent.

[2] The therapeutic agent for FIV infections, wherein the feline interferon is a a feline ω-interferon.

[3] The therapeutic agent for feline AIDS virus infections, wherein the feline ω-interferon is a recombinant interferon.

[4] The therapeutic agent for FIV infections, wherein the feline ω-interferon is a glycosylated interferon having the amino acid sequence shown in SEQ ID NO:1.

[5] The therapeutic agent for FIV infections, according to any one of [1] through [4], which is used for treating anemia caused by infection with FIV.

[6] The therapeutic agent for FIV infections, according to any one of [1] through [4], which is used for treating chronic stomatitis caused by infection with FIV.

[7] A therapeutic method for FIV infections, comprising the step of administering a feline interferon preparation containing a feline interferon as a principal agent to a cat continuously every day.

[8] The therapeutic method for FIV infections, wherein the feline interferon is a feline ω-interferon.

[9] The therapeutic method for FIV infections, wherein the feline ω-interferon is a recombinant interferon.

[10] The therapeutic method for FIV infections, wherein the feline ω-interferon is a glycosylated interferon having the amino acid sequence shown in SEQ ID NO:1.

[11] The therapeutic method for FIV infections, according to any one of [7] through [10], which is used for treating anemia caused by infection with FIV.

[12] The therapeutic method for FIV infections, according to any one of [7] through [10], which is used for treating chronic stomatitis caused by infection with FIV.

[13] The therapeutic method for FIV infections, according to any one of [7] through [12], wherein the feline ω-interferon is administered as a dose of 0.5 MU/kg~2.5 MU/kg per cat body weight once or more per day for 5 or more consecutive days.

[14] A therapeutic agent for feline atopic dermatitis, comprising a feline interferon.

[15] The therapeutic agent for feline atopic dermatitis, wherein the feline interferon is a feline ω-interferon.

[16] The therapeutic agent for feline atopic dermatitis, wherein the feline ω-interferon is a recombinant interferon.

[17] The therapeutic agent for feline atopic dermatitis, according to [15] or [16], wherein the feline ω-interferon is a glycosylated interferon having the amino acid sequence shown by SEQ ID NO:1.

[18] The therapeutic method for feline atopic dermatitis, wherein the therapeutic agent for atopic dermatitis stated in any one of [14] through [17] is injected into a cat.

[19] The therapeutic method for feline atopic dermatitis, wherein the injection is a subcutaneous injection.

[20] The therapeutic method for feline atopic dermatitis, wherein the injection dose is 0.1 –5 MU/kg.

THE BEST EMBODIMENTS OF THE INVENTION

It is preferable that the feline interferon used in the present invention is a feline ω-interferon which can be as produced naturally, synthetically synthesized, or produced by any gene recombination technique.

For example, a feline ω-interferon produced by a genetic recombination and marketed under a trade name of "INTERCAT"(produced by Toray Industries, Inc.) can be used.

"INTERCAT" has been approved and practically applied as a therapeutic agent for feline calicivirus infections, and mainly contains a glycosylated interferon having the sequence of 170 amino acids shown in SEQ ID NO:1, and it is obtained by infecting larvae of *Bombyx mori* with a recombinant baculovirus, (i.e., an insect virus recombined with the gene of a feline ω-interferon), and extracting, separating and refining the interferon produced in *Bombyx mori*.

However, the feline ω-interferon of the present invention is not necessarily limited to recombinant feline interferon.

The ω-feline interferons produced by gene manipulation using bacterial cells (such as Escherichia coli and Bacillus subtilis) animal cells (such as CHO) and also the ω-interferon produced from feline cells can be used. However, presently, the feline ω-interferon produced from *Bombyx mori* is available at low cost.

First, the therapeutic method for FIV infections is described. The therapeutic method is to inject a therapeutic agent containing a feline ω-interferon into a cat once or more per day for 5 or more consecutive days. The dose of the feline interferon is 0.5 MU/kg~2.5 MU/kg per cat body weight.

It is practical to administer the therapeutic agent once a day. It can be administered once or more per day, but it is preferable to administer at least once a day. It is desirable to administer every day, instead of every other day, and it is more desirable to administer continuously for 5 days or more.

After administering for 5 consecutive days or more, the administration can be once suspended, and subsequently administration can be effected again for 5 or more consecutive days.

The dose can also be smaller than 0.5 MU/kg, but if the dose is smaller than 0.5 MU/kg, the therapeutic effect is also weaker. On the contrary, even if the dose is larger than 2.5 MU/kg, the therapeutic cost simply increases, without giving any correspondingly higher effect in most cases.

The injection route can be subcutaneous or intravenous. Intramuscular injection can also be used. However, subcutaneous injection can be practically and simply effected. When the therapeutic method of the present invention was used for treating the anemia as one of feline AIDS virus symptoms, recovery from lethargy and increase of appetite could be achieved, and erythroid values such as erythrocyte number, hemoglobin and hematocrit increased.

When used to treat chronic stomatitis, the stomatitis accompanying the ulcers and granulomata of fauces improved and appetite and vitality were restored.

Feline atopic dermatitis it described below. The therapeutic agent for feline atopic dermatitis of the present invention is a preparation containing a feline ω-interferon as a principal agent, and when it is used, a solution obtained by dissolving it into physiologic salt solution or infusion solution or any other solution is injected. The injection route can be subcutaneous, intravenous or in tramuscular. Subcutaneous injection is preferably simple and practical. The number of administrations is not especially limited, but it is practical to administer once a day every day or 1 to 3 times per week. The dose is not limited either, but is usually 0.1 to 5 MU/kg. A preferable range is 1 to 2.5 MU/kg. The administration effect can be clearly observed from about the 2nd week in most cases.

The feline ω-interferons usually do not cause remarkable fever after administration unlike in human beings, and even if fever occurs, body temperature elevation as slight as about 1° C. only occurs for a while. Serious side effects such as vomition and diarrhea do not occur.

EXAMPLES

The present invention is described below in reference to examples, but is not limited thereto or thereby. The blood cell count is in number of cells per microliter ($/\mu l$).

Example 1

A recombinant feline ω-interferon preparation (trade name: INTERCAT) was administered to a Japanese cat (female) of 3 to 4 years of age that had been suffering from anemia caused by FIV infection. On the day of the first medical examination, the body weight was 3.7 kg, and she had lost appetite from the previous day, remained lethargic and showed pale mucous membranes.

1.85 ml tetracycline was subcutaneously injected, and a 500 ml vitamin preparation was subcutaneously dripped. On the following day, the body weight became 4.0 kg. By a virus check, she was positive for anti-FIV antibody and negative for FeLV antigen. Blood examination values were WBC 12,600, erythrocytes 144,000, hemoglobin 3.7 g/dl, hematocrit 12.3%, mean cell volume (MCV) 85 fl, mean cell hemoglobin concentration (MCHC) 30.1 g/dl and thrombocytes 163,000.

INTERCAT was dissolved into physiological salt solution, and the INTERCAT solution was subcutaneously injected by 10 MU/day for 3 days. The dose per body weight was 2.5 MU/kg. A 500 ml/day infusion solution (vitamin preparation) was subcutaneously dripped, and a 1.85 ml antibiotic (tetracycline) was subcutaneously injected.

Prom the 4th day, INTERCAT was decreased to 4 MU/day, and subcutaneously injected for 4 days. The dose per body weight was 0.75 MU/kg.

On the 5th day, appetite was restored a little.

On the 8th day, blood examination values were WBC 10,400, erythrocytes 358, hemoglobin 4.9 g/dl, hematocrit 28.5 %, mean cell volume (MCV) 65 fl, mean cell hemoglobin concentration (MCHC) 30.2 g/dl and thrombocytes 178,000. The body weight was 3.4 kg.

Even after the 85th day, vitality and appetite remained normal. The blood examination values were WBC 11,400, erythrocytes 971, hemoglobin 11.8 g/dl, hematocrit 40.3%, mean cell volume (MCV) 42 fl, mean cell hemoglobin concentration (MCHC) 29.3 g/dl and thrombocytes 198,000. The body weight was 3.9 kg.

Example 2

A recombinant feline ω-interferon preparation (trade name: INTERCAT) was administered to a Japanese cat (male) of 6 to 7 years old who had been suffering from anemia caused by infection with FIV. On the day of the first medical examination, the body weight was 7.55 kg. Appetite had declined from the previous day, and he was lethargic.

By a virus test, he was positive for anti-FIV antibody and negative for FeLV antigen. An anti-inflammatory drug, loxoprofen sodium was administered (½ tablet twice a day). The blood examination values were WBC 3,500, erythrocytes 3,670,000, hemoglobin 5.3 g/dl, hematocrit 18.4%, mean cell volume (MCV) 50 fl, mean cell hemoglobin concentration (MCHC) 31.5 g/dl and thrombocytes 105,000.

INTERCAT was dissolved into physiological salt solution, and 10 MU/day of the INTERCAT solution was subcutaneously injected for 3 days. On the 4th day, the dose was decreased to 2.5 MU/day, and the INTERCAT solution was subcutaneously injected for further 3 days. From the 7th day, the dose was increased to 10 MU/day, and the INTERCAT solution was subcutaneously injected for 3 days.

On the 9th day, the blood test values were WBC 10,600, erythrocytes 4,020,000, hemoglobin 6.4 g/dl, hematocrit 21.0%, mean cell volume (MCV) 52 fl, mean cell hemoglobin concentration (MCHC) 30.5 g/dl and thrombocytes 351,000. Appetite was restored a little. The body weight was 7.3 kg.

On the 18th day, he came to hospital again due to anorexia. The body weight was 7.05 kg. The blood examination values were WBC 6,900, erythrocytes 10,430,000, hemoglobin 16.0 g/dl, hematocrit 51.7%, mean cell volume (MCV) 50 fl, mean cell hemoglobin concentration (MCHC) 30.9 g/dl and thrombocytes 324,000.

A 10 MU/day solution of INTERCAT was subcutaneously injected for 7 days. An antibiotic (Baytril) was administered (½ tablet twice a day). Infusion was effected on the 18th day only. Even after one month, vitality and appetite remained recovered.

Example 3

A recombinant feline ω-interferon preparation (trade name: INTERCAT) was administered to a 10-year-old Japanese cat (male) who had been suffering from chronic stomatitis caused by FIV infection. On the day of the first medical examination, the body weight was 4.6 kg, and saliva and the ulcers and granulomata of fauces on both sides were observed. By a virus test, he was positive for anti-FIV antibody and negative for FeLV antigen.

INTERCAT was dissolved in physiological salt solution, and 10 MU/day of the INTERCAT solution was subcutaneously injected for 3 days. The dose per body weight was 2.17 MU/kg. After the 4th day, the dose was decreased to 4 MU/day, and the INTERCAT solution was subcutaneously injected for 4 more days. Only on the 2nd day, a 500 ml infusion solution (vitamin preparation) was subcutaneously dripped. An antibiotic (Baytril) was administered every day.

On the 3rd day, appetite was restored a little. Saliva was also improved a little. As for the stomatitis, the granuloma on the left side became slightly less reddish.

On the 4th day, as for the stomatitis, the granuloma on the left side was reduced in size and reddishness.

On the 5th day, as for the stomatitis, the granuloma on the right side vanished, and the granuloma on the left side was further reduced in reddishness.

On the 7th day, appetite was restored, and as for the stomatitis, ulcers and granulomat vanished. On the 10th day, the body weight was 4.95 kg.

Even after six months, the stomatitis was not worsened.

Example 4

A recombinant feline ω-interferon preparation (trade name: INTERCAT) was administered to an 8-year-old Japanese cat (male) who had been suffering from chronic stomatitis caused by infection with FIV. On the day of the first medical examination, the body weight was 3.4 kg, and saliva and ulcers and granulomata of fauces on both sides were observed. By a virus test, he was positive for anti-FIV antibody and negative for FeLV antigen.

INTERCAT was dissolved into physiological salt solution, and 8.5 MU/day of the INTERCAT solution was subcutaneously injected for 7 days. The dose per body weight was 2.5 MU/kg.

After the 8th day, the dose was decreased to 4 MU/day, and the INTERCAT solution was subcutaneously injected for 4 more days. On the 2nd day only, a 300 ml infusion solution (vitamin preparation) was subcutaneously dripped. Antibiotics (Dalacin; clindamycin) were administered every day.

On the 7th day, appetite was restored. The body weight was 3.75 kg. Saliva improved, and the stomatitis also improved.

After two months, the stomatitis was not especially worsened, but 2.5 MU/kg INTERCAT was subcutaneously injected for 7 days.

After six months, the stomatitis was not worsened.

Example 5

A 4-year-old spayed female house cat (short hair, Japanese cat) (white, body weight 2.62 kg) came to the hospital primarily for the main reason that red eczema occurred in the abdominal area several days before, and she was diagnosed with atopic dermatitis. A preparation containing a feline ω-interferon (recombinant) as a principal agent, i.e., "INTERCAT" was dissolved into physiological solution, and a 5 MU/ead (1.9 MU/kg) of the INTERCAT solution was subcutaneously injected. The administration of "INTERCAT" was continued at intervals of twice a week. After 8 weeks, the eczema perfectly vanished.

Example 6

A 3-year-old female house cat (Cornish Rex) (white, body weight 2.76 kg) had eosinophilic plaques formed with the hypertrophy of the dorsolumbar skin since several months before, and was cured temporarily by periodic administration of a steroid hormone preparation. However, after a while, many plaques occurred on the face and the back. On the auricles, portions showing the presence of a fungus existed. The disease was diagnosed as atopic dermatitis. A preparation containing a feline 107-interferon (recombinant) as a principal agent, i.e., "INTERCAT" was dissolved into physiological salt solution, and 5 MU/head (1.81 MU/kg) of the INTERCAT solution was subcutaneously injected. An antihistaminic agent previously used was also used. The administration of "INTERCAT" was continued at intervals of once a week. From the 2nd week, the reddishness of the eczema began to vanish, and after 3 months, only a trace remained, showing an almost perfect healing.

Example 7

A 6-year-old spayed female house cat (short hair, Japanese cat) (blackish tiger color, body weight 4.55 kg) had had miliary eczema on the back due to flea allergy since two years before, and the administration of a steroid hormone preparation and thorough flea extermination brought about a lesion. However, since about one year before, many eosinophilic plaques were formed in the abdominal area, and although the administration of the steroid hormone preparation showed an effect, the effect gradually diminished. The disease was diagnosed as atopic dermatitis. A preparation containing a feline ω-interferon (recombinant) as a principal agent, i.e., "INTERCAT" was dissolved into physiological salt solution, and 5 MU/head (1. 1 MU/kg) of the INTERCAT solution was subcutaneously injected. The administration of "INTERCAT" continued at intervals of once a week. After 2 weeks, reddishness almost vanished, and even after 2 months, the disease did not recur.

Industrial Applicability

The present invention is an effective therapeutic agent containing a feline ω-interferon, for treating anemia and chronic stomatitis caused by FIV infection (confirmed by a virus test of feline blood showing anti-FIV antibody), and also is an effective therapeutic method using said therapeutic agent. Furthermore, the therapeutic agent containing a feline ω-interferon is a new excellent therapeutic agent and method for feline atopic dermatitis. The present invention is highly industrially useful.

What is claimed is:

1. A method for ameliorating symptoms associated with FIV infections, comprising administering a preparation containing an effective amount of a feline ω-interferon as a principal agent to a cat infected with FIV for a time and under conditions sufficient to ameliorate symptoms associated with FIV infections.

2. The method according to claim 1, wherein said feline ω-interferon is a recombinant ω-interferon.

3. The method according to claim 1, wherein said feline ω-interferon is a glycosylated interferon having the amino acid sequence shown in SEQ ID NO:1.

4. The method a according to claim 1, wherein said ω-interferon is administered for treating anemia caused by infection with FIV.

5. The method according to claim 1, wherein said ω-interferon is administered for treating chronic stomatitis caused by infection with FIV.

6. The method according to claim 1, wherein said feline ω-interferon is administered at a dose of 0.5 MU/kg~2.5 MU/kg per cat body weight, at least once per day for at least 5 consecutive days.

7. A therapeutic method for ameliorating symptoms associated with feline atopic dermatitis comprising administering an effective amount of a feline ω-interferon to a cat suffering from atopic dermatitis for a time and under conditions sufficient to ameliorate symptoms associated with feline atopic dermatitis.

8. The method according to claim 7 wherein said feline ω-interferon is administered by subcutaneous injection.

9. The method according to claim 7 wherein said feline ω-interferon is administered at a dose of 0.1~5 MU/kg.

* * * * *

UNITED STATES PATENT AND TRADEMARK OFFICE
CERTIFICATE OF CORRECTION

PATENT NO.     : 6,194,381 B1
DATED          : February 27, 2001
INVENTOR(S)    : Kajimoto et al It is certified that error appears in the above-identified patent and that said Letters Patent is hereby corrected as shown below:

<u>Column 2,</u>
Line 13, please change "107" to -- $\omega$ --.

Signed and Sealed this

Thirtieth Day of October, 2001

Attest:

NICHOLAS P. GODICI
*Attesting Officer*     *Acting Director of the United States Patent and Trademark Office*

SEQUENCE LISTING

<160> NUMBER OF SEQ ID NOS: 1

<210> SEQ ID NO 1
<211> LENGTH: 170
<212> TYPE: PRT
<213> ORGANISM: Felis catus

<400> SEQUENCE: 1

Cys Asp Leu Pro Gln Thr His Gly Leu Leu Asn Arg Arg Ala Leu Thr
 1               5                  10                  15

Leu Leu Gly Gln Met Arg Arg Leu Pro Ala Ser Ser Cys Gln Lys Asp
            20                  25                  30

Arg Asn Asp Phe Ala Phe Pro Gln Asp Val Phe Gly Gly Asp Gln Ser
        35                  40                  45

His Lys Ala Gln Ala Leu Ser Val Val His Val Thr Asn Gln Lys Ile
    50                  55                  60

-continued

```
Phe His Phe Phe Cys Thr Glu Ala Ser Ser Ala Ala Trp Asn Thr
 65              70              75              80

Thr Leu Leu Glu Glu Phe Cys Thr Gly Leu Asp Arg Gln Leu Thr Arg
             85              90              95

Leu Glu Ala Cys Val Leu Gln Glu Val Glu Glu Gly Glu Ala Pro Leu
            100             105             110

Thr Asn Glu Asp Ile His Pro Glu Asp Ser Ile Leu Arg Asn Tyr Phe
        115             120             125

Gln Arg Leu Ser Leu Tyr Leu Gln Glu Lys Lys Tyr Ser Pro Cys Ala
        130             135             140

Trp Glu Ile Val Arg Ala Glu Ile Met Arg Ser Leu Tyr Tyr Ser Ser
145             150             155             160

Thr Ala Leu Gln Lys Arg Leu Arg Ser Glu
            165             170
```